United States Patent
Akselrod-Ballin et al.

(10) Patent No.: US 10,878,569 B2
(45) Date of Patent: Dec. 29, 2020

(54) SYSTEMS AND METHODS FOR AUTOMATIC DETECTION OF AN INDICATION OF ABNORMALITY IN AN ANATOMICAL IMAGE

(71) Applicant: International Business Machines Corporation, Armonk, NY (US)

(72) Inventors: Ayelet Akselrod-Ballin, Kiryat-Ono (IL); Ran Bakalo, Haifa (IL); Rami Ben-Ari, Kiryat-Ono (IL); Yoni Choukroun, Tel Aviv (IL); Pavel Kisilev, Maalot (IL)

(73) Assignee: International Business Machines Corporation, Armonk, NY (US)

( * ) Notice: Subject to any disclaimer, the term of this patent is extended or adjusted under 35 U.S.C. 154(b) by 353 days.

(21) Appl. No.: 15/937,884

(22) Filed: Mar. 28, 2018

(65) Prior Publication Data
US 2019/0304092 A1    Oct. 3, 2019

(51) Int. Cl.
*G06K 9/00* (2006.01)
*G06T 7/00* (2017.01)
(Continued)

(52) U.S. Cl.
CPC .......... *G06T 7/0014* (2013.01); *G06K 9/2054* (2013.01); *G06K 9/6259* (2013.01);
(Continued)

(58) Field of Classification Search
None
See application file for complete search history.

(56) References Cited

U.S. PATENT DOCUMENTS 6,125,194 A    9/2000 Yeh et al.
7,738,683 B2   6/2010 Cahill et al.
(Continued)

FOREIGN PATENT DOCUMENTS

CN    106682435    5/2017

OTHER PUBLICATIONS

Chatfield, Ken, et al. "Return of the devil in the details: Delving deep into convolutional nets." arXiv preprint arXiv:1405.3531 (2014). (Year: 2014).*
(Continued)

*Primary Examiner* — Sean M Conner
(74) *Attorney, Agent, or Firm* — G. E. Ehrlich

(57) ABSTRACT

There is provided a method for training a deep convolutional neural network (CNN) for detecting an indication of likelihood of abnormality, comprising: receiving anatomical training images, each including an associated annotation indicative of abnormality for the whole image without an indication of location of the abnormality, executing, for each anatomical training image: decomposing the anatomical training image into patches, computing a feature representation of each patch, computing for each patch, according to the feature representation of the patch, a probability that the patch includes an indication of abnormality, setting a probability indicative of likelihood of abnormality in the anatomical image according to the maximal probability value computed for one patch, and training a deep CNN for detecting an indication of likelihood of abnormality in a target anatomical image according to the patches of the anatomical training images, the one patch, and the probability set for each respective anatomical training image.

18 Claims, 7 Drawing Sheets

(51) Int. Cl.
*G06N 3/08* (2006.01)
*G16H 30/20* (2018.01)
*G06K 9/62* (2006.01)
*G06T 7/13* (2017.01)
*G06T 7/143* (2017.01)
*G06T 7/62* (2017.01)
*G06K 9/20* (2006.01)
*G06N 7/00* (2006.01)

(52) U.S. Cl.
CPC ......... *G06K 9/6261* (2013.01); *G06K 9/6277* (2013.01); *G06N 3/08* (2013.01); *G06N 7/005* (2013.01); *G06T 7/13* (2017.01); *G06T 7/143* (2017.01); *G06T 7/62* (2017.01); *G16H 30/20* (2018.01); *G06K 2209/05* (2013.01); *G06T 2207/20076* (2013.01); *G06T 2207/20081* (2013.01); *G06T 2207/20084* (2013.01); *G06T 2207/30068* (2013.01)

(56) References Cited

U.S. PATENT DOCUMENTS

| | | |
|---|---|---|
| 9,589,374 B1 | 3/2017 | Gao et al. |
| 9,760,807 B2 | 9/2017 | Zhou et al. |
| 2016/0174902 A1 | 6/2016 | Georgescu et al. |
| 2018/0075628 A1* | 3/2018 | Teare ..................... A61B 6/461 |
| 2019/0087532 A1* | 3/2019 | Madabhushi ........ G06K 9/4628 |
| 2019/0150867 A1* | 5/2019 | Itou ........................ A61B 6/504 |
| 2020/0065974 A1* | 2/2020 | Guo .......................... G06T 7/13 |
| 2020/0066407 A1* | 2/2020 | Stumpe .................. G06F 15/76 |
| 2020/0085382 A1* | 3/2020 | Taerum ................. G06N 3/084 |

OTHER PUBLICATIONS

Hwang et al., "Self-Transfer Learning for Fully Weakly Supervised Object Localization", arxiv, 2016.

Shin et al., "Joint Weakly and Semi-Supervised Deep Learning for Localization and Classification of Masses in Breast Ultrasound Images", arxiv, 2017.

Choukroun et al., "Mammogram Classification and Abnormality Detection from Nonlocal Labels using Deep Multiple Instance Neural Network", Eurographics Workshop on Visual Computing for Biology and Medicine, 2017.

Quellec et al., "Multiple-Instance Learning for Anomaly Detection in Digital Mammography", IEEE Transactions on Medical Imaging, Jul. 2016, pp. 1604-1614, vol. 35, Issue 7.

Zhu et al., "Deep Multi-instance Networks with Sparse Label Assignment for Whole Mammogram Classification", arxiv, Dec. 18, 2016.

* cited by examiner

US 10,878,569 B2

SYSTEMS AND METHODS FOR AUTOMATIC DETECTION OF AN INDICATION OF ABNORMALITY IN AN ANATOMICAL IMAGE

BACKGROUND

The present invention, in some embodiments thereof, relates to automatic detection of indication of abnormality in anatomical images and, more specifically, but not exclusively, to systems and methods for training a convolutional neural network (CNN) for automatic detection of indication of abnormality in an anatomical image.

Cancer is a leading cause of death. Cancer may be suspected and/or diagnosed by a radiologist analyzing anatomical images of a target organ. Manual analysis of image is tedious, time consuming, and prone to errors, for example, mistaking a benign anatomical feature for malignancy (which may lead to an unnecessary biopsy), or missing a malignancy entirely.

The most common cancer and second leading cause of death among women is breast cancer for example, as described with reference to by Ahmedin Jemal, Freddie Bray, Melissa M Center, Jacques Ferlay, Elizabeth Ward, and David Forman. *Global cancer statistics. CA: a cancer journal for clinicians*, 61(2):69-90, 2011, where the medical community is striving for its early detection. Mammography is commonly used for screening and detection of breast cancer, for example, as described with reference to Blake Cady and Maureen Chung. *Mammographic screening: no longer controversial. American journal of clinical oncology*, 28(1):1-4, 2005. In current practice, the radiologists and CADx systems follow a two stage process defined by the detection of abnormalities followed by their classification according to the standard Breast Imaging Reporting and Data System (BI-RADS). Medical image analysis, for example, mammogram analysis, is challenging, due to the high variability of tissue (e.g., breast) patterns and variations in appearance, size and shape of the abnormalities, making them often difficult to detect and classify, even by expert radiologists.

SUMMARY

According to a first aspect, a computer implemented method for training a deep convolutional neural network (CNN) for detecting an indication of likelihood of abnormality in a target anatomical image based on a plurality of anatomical training images each associated with an annotation for a whole respective training image, comprises: receiving a plurality of anatomical training images, each including an associated annotation indicative of abnormality for the whole respective anatomical training image without an indication of a location of the abnormality within the respective anatomical image, executing, for each respective anatomical training image of the plurality of anatomical training images: decomposing the respective anatomical training image into a plurality of patches, computing a feature representation of each patch of the plurality of patches, computing for each respective patch of the plurality of patches, according to the feature representation of the respective patch, a probability that the respective patch includes an indication of abnormality, setting a probability indicative of likelihood of abnormality in the respective anatomical image according to the maximal probability value computed for one patch of the plurality of patches, and training a deep convolutional neural network for detecting an indication of likelihood of abnormality in a target anatomical image according to the plurality of patches of the plurality of anatomical training images, the one patch, and the probability set for each respective anatomical training image.

According to a second aspect, a system for training a deep CNN for detecting an indication of likelihood of abnormality in a target anatomical image based on a plurality of anatomical training images each associated with an annotation for a whole respective training image, comprises: a non-transitory memory having stored thereon a code for execution by at least one hardware processor of a computing device, the code comprising: code for receiving a plurality of anatomical training images, each including an associated annotation indicative of abnormality for the whole respective anatomical training image without an indication of a location of the abnormality within the respective anatomical image, code for executing, for each respective anatomical training image of the plurality of anatomical training images: decomposing the respective anatomical training image into a plurality of patches, computing a feature representation of each patch of the plurality of patches, computing for each respective patch of the plurality of patches, according to the feature representation of the respective patch, a probability that the respective patch includes an indication of abnormality, setting a probability indicative of likelihood of abnormality in the respective anatomical image according to the maximal probability value computed for one patch of the plurality of patches, and code for training a deep convolutional neural network for detecting an indication of likelihood of abnormality in a target anatomical image according to the plurality of patches of the plurality of anatomical training images, the one patch, and the probability set for each respective anatomical training image.

According to a third aspect, a computer implemented method for detecting an indication of likelihood of abnormality in a target anatomical image, comprises: receiving the target anatomical image, decomposing the target anatomical training image into a plurality of patches, computing a feature representation of each patch of the plurality of patches by a deep CNN trained based on a plurality of anatomical training images each associated with an annotation for a whole respective training image without an indication of a location of the abnormality within the respective anatomical image, computing by the deep CNN, for each respective patch of the plurality of patches, according to the feature representation of the respective patch, a probability that the respective patch includes an indication of abnormality, and setting a probability indicative of likelihood of abnormality in the target anatomical image according to the maximal probability value computed for one of the plurality of patches.

Some implementations of the systems and/or methods and/or apparatus and/or code instructions described herein address the technical problem of training a deep CNN to detect an indication of abnormality in a target anatomical image according to a set of weakly labeled anatomical images.

In the weakly supervised paradigm described herein, only image-level tags are necessary to train a classifier, as opposed to fully supervised classification and detection, which typically requires exhaustive annotations of the medical images. Such annotation which is commonly performed manually is a source of additional errors, which leads to a reduction in accuracy of the trained classifier. Annotation may be incomplete, resulting in ambiguous lesion margins that create controversial annotations, which may lead to a reduction in accuracy of the trained classifier.

Some implementations of the systems and/or methods and/or apparatus and/or code instructions described herein improve performance of a computing device that trains the deep CNN based on the weakly labeled set of anatomical images. The improvement in performance may be based on an increase in accuracy of detecting the indication of abnormality using existing computing resources (e.g., processor (s), and/or data storage), and/or improving the efficiency of detecting the indication of abnormality by a reduction in processing time, a reduction in processor utilization, and/or a reduction in data storage requirements. As described in additional detail in the Examples section below, the systems, method, apparatus, and/or code instructions described herein yields a high performance in terms of AUC, comparing several other methods in the literature Some implementations of the systems and/or methods and/or apparatus and/or code instructions described herein may train the deep convolutional neural network to perform the classification of the anatomical image using high accuracy, using a weakly labeled training set. The systems, methods, apparatus, and/or code instructions described herein may utilize previously obtained anatomical images and radiology interpretation reports to train the deep CNN, without requiring manual annotation by an expert. It is noted that such manual annotation may be unavailable, difficult to obtain, and/or costly to obtain. The accuracy of the deep CNN may be improved by utilizing relatively larger number of anatomical images as training images, without incurring the costs associated with manual annotation. For example, anatomical images and associated whole image annotation may be extracted from existing databases, for example, from a PACS server and/or EMR server.

The deep CNN is trained relatively quickly to provide the location of the identified indication of abnormality, since training a localizer to perform the localization is not explicitly performed. Localization is acquired automatically as a by-product, according to the location within the anatomical image of the patch having highest probability indicative of abnormality.

In another example, the trained deep CNN that is applied to classify a anatomical image performs the classification within a relatively short processing time, using relatively fewer processing resources, and/or using relatively smaller data storage requirements. The improvement in performance may include training the deep CNN and/or applying the deep CNN using less memory, and/or using fewer computational resources (e.g., processor(s) utilization), and/or faster computation time, without sacrificing the accuracy (and in many cases improving the accuracy) of the identifying of abnormality within the image.

The exemplary architecture of the trained CNN described herein improves computational efficiency of the computing device training the deep CNN, for example in terms of reduced processing time, reduced utilization of computational resources, and/or reduced data storage requirements. The improvement in computational efficiency arises, for example, since the patch feature vectors are computed only a single time during a training round by the first stage of the deep CNN, and/or since the second stage includes a small number (e.g., 3 or other value, such as 4, or 4) of fully connected layers.

Some implementations of the systems, methods, apparatus, and/or code instructions described herein do not simply perform automation of a manual procedure, but perform additional automated features which cannot be performed manually by a human using pencil and/or paper. The deep CNN described herein automatically extracts features from the decomposed patches described herein to compute the classification result, which is an entirely different process than that performed by a human interpreter.

The deep CNN described herein may be trained automatically without necessarily requiring human intervention, as no handcrafted features are needed (features are automatically computed and extracted), and no manual annotation of the location of the abnormality within the anatomical image is required (the whole image indication may be automatically extracted from the medical record and/or associated radiology report).

The decomposition of the image into patches allows processing the high resolution image without scarifying the original resolution. Some implementations of the systems and/or methods and/or apparatus and/or code instructions described herein are insensitive to the image size and/or to the number of patches extracted from the image. There is no requirement to wrap the image to a fixed size (as performed by some other methods) which causes the distortion of the image and/or distortion of the lesion. The patch based approach described by some implementations of the systems and/or methods and/or apparatus and/or code instructions described herein allows processing of non-rectangular regions in the image by masking of certain areas, by excluding patches. A combined pre-trained CNN according to some implementations of the systems and/or methods and/or apparatus and/or code instructions described herein allows training on small data sets while shortening the training duration, since only the fully connected layers are trained.

In a further implementation form of the method or the system according to the first or second aspects, an abnormality appearing in each one of the plurality of anatomical training images is not associated with a manual annotation indicative of location of the abnormality within the respective anatomical training image.

In a further implementation form of the method or the system according to the first or second aspects, the deep CNN is trained according to a loss function that considers the one patch of the plurality of patches most probably indicative of abnormality and excludes other patches of the plurality of patches with lower probability values than the one patch, wherein the one patch is back propagated through the deep CNN for updating of the plurality of coefficients of the deep CNN.

In a further implementation form of the method or the system according to the first or second aspects, the deep CNN is trained according to a loss function that computes a log likelihood loss according to a probability that a certain patch of the plurality of patches is classified as indicative of abnormality based on a plurality of coefficients of the deep CNN.

In a further implementation form of the method or the system according to the first or second aspects, the loss function is mathematically represented as:

$$\mathcal{L}(\theta) = \sum_{\substack{X_i \in \Lambda \\ Y_i = y_+}} \log\left(\max_{x_{ij} \in X_i} \mathbb{P}(y_+ \mid x_{ij}, \theta)\right) + \sum_{\substack{X_i \in \Lambda \\ Y_i = y_-}} \log\left(1 - \max_{x_{ij} \in X_i} (\mathbb{P}(y_+ \mid x_{ij}, \theta))\right)$$

wherein:

$x_{ij}$ denotes the respective patch of the respective anatomical image,

θ denotes the coefficients of the deep CNN, $\mathbb{P}(y_+|x_{ij},\theta)$ denotes a probability that the respective patch denoted $x_{ji}$ is classified as positive based on the coefficients θ of the deep CNN.

In a further implementation form of the method or the system according to the first or second aspects, the probability comprises a probabilistic geometric prior value denoting areas on a border of at least one tissue portion based on distance from an edge of the area on the border of the at least one tissue portion.

In a further implementation form of the method or the system according to the first or second aspects, the geometric prior value is mathematically represented as:

$$\omega(x_{ij}) = 1 - \frac{\mathcal{A}(x_{ij} \cap \mathcal{B})}{\mathcal{A}(x_{ij})}$$

where:

$\omega(x_{ij})$ denotes the geometric prior value, $\mathcal{A}(x_{ij})$ denotes the area of the respective patch of the respective anatomical image $x_{ij}$, and β denotes the area on the border of the at least one tissue portion.

In a further implementation form of the method or the system according to the first or second aspects, the size of each of the plurality of anatomical training images is at least one of arbitrary and varying between each of the plurality of anatomical training images, and wherein a number of the plurality of patches is at least one of arbitrary and varying between each of the plurality of anatomical training images.

In a further implementation form of the method or the system according to the first or second aspects, the respective anatomical training image is decomposed based on a sliding window moved within the respective anatomical training image to extract each of the plurality of patches, wherein the each patch of the plurality of patches overlaps with at least one other patch of the plurality of patches.

In a further implementation form of the method or the system according to the first or second aspects, the plurality of patches are decomposed from the respective anatomical training image in full resolution and without downsampling.

In a further implementation form of the method or the system according to the first or second aspects, the trained deep CNN comprises a first stage including a pretrained CNN, wherein the trained deep CNN coefficients are extracted from a last hidden layer of the pretrained CNN, and a second stage comprising a refined fully connected neural network comprising three fully connected layers trained from scratch according to a loss function that considers the one patch of the plurality of patches and back propagates the one patch through the refined fully connected neural network.

In a further implementation form of the method or the system according to the first or second aspects, the trained deep CNN coefficients extracted from the last hidden layer of the first stage are represented as a 4096D feature vector, wherein the feature representation of each patch comprises the 4096D feature vector.

In a further implementation form of the method or the system according to the first or second aspects, the refined fully connected neural network computes for each respective patch of the plurality of patches, according to the corresponding feature vector, the probability that the respective patch includes an indication of abnormality.

In a further implementation form of the method or the system according to the first or second aspects, the convolutional neural network coefficients extracted from the last hidden layer of the first stage are computed once for each patch of the plurality of patches.

In a further implementation form of the method or the system according to the first or second aspects, the three fully connected layers of the refined fully connected neural network comprise rectified linear units (ReLUs) as nonlinear layers, and wherein the second stage is optimized using momentum stochastic gradient descent.

In a further implementation form of the method or the system according to the first or second aspects, the plurality of anatomical images comprise a plurality of mammographic training images, each including at least one breast portion.

In a further implementation form of the method according to the third aspect, the method further comprises providing an indication of a location indicative of likelihood of abnormality according to the location with the target anatomical image of at least one patch of the plurality of patches associated with the maximal probability value.

In a further implementation form of the method according to the third aspect, the method further comprises presenting on a display, the target anatomical with a plurality of overlay markings each indicative of the location of one of the plurality of patches within the anatomical image according to decreasing probability values, wherein each overlay marking distinctly represents a descending order of probability, wherein each overlay indicates abnormality location in full resolution.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
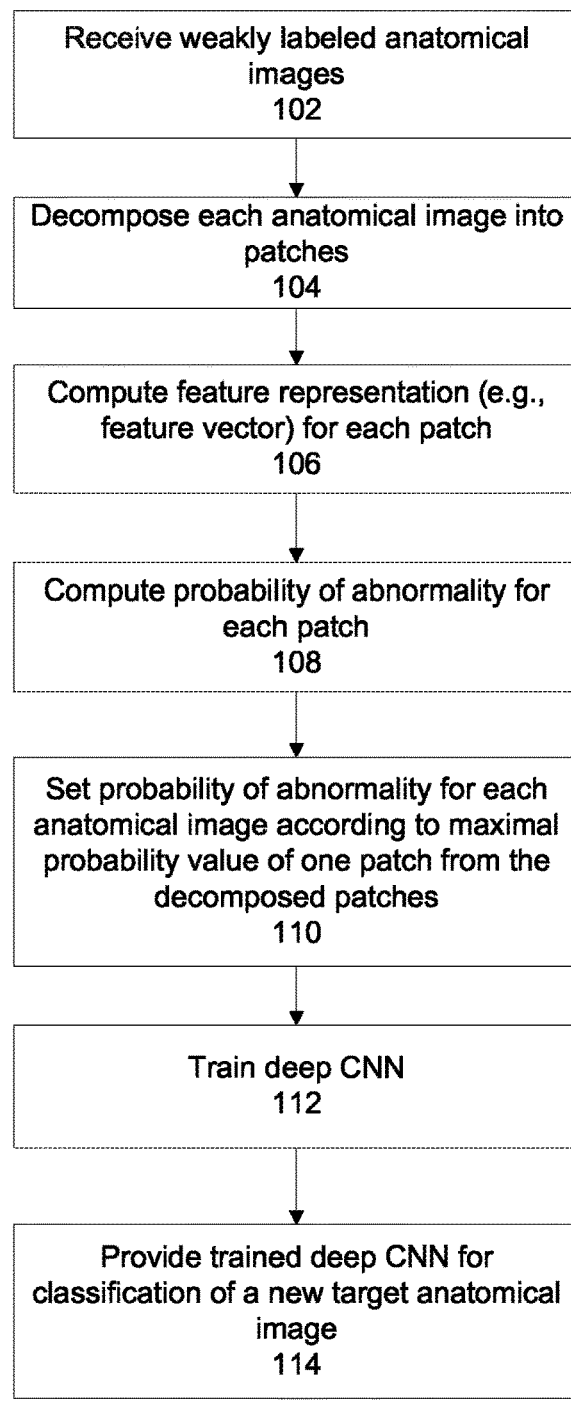
FIG. 1 is a flowchart of a method for training a deep convolutional neural network according to a weakly labeled set of anatomical training images, in accordance with some embodiments of the present invention.

The present invention, in some embodiments thereof, relates to automatic detection of indication of abnormality (e.g., malignancy, benign) in anatomical images and, more specifically, but not exclusively, to systems and methods for training a convolutional neural network (CNN) for automatic detection of indication of abnormality in a anatomical image.

As used herein, the term anatomical image means an image depicting an intra-body anatomical structure of an individual, for example, a breast image, a chest image, an abdominal image, a pelvic image, and an image of a limb. The anatomical images are captured by an anatomical imaging modality, for example, a CT scanner, an MRI machine, an x-ray machine, and an ultrasound machine.

The reference made herein to detection of abnormalities in mammographic images of the breast represents an exemplary implementation that is not necessarily limiting. Other anatomical images of other body parts and/or other imaging modalities may be similarly processed, for example, chest CTs to identify abnormalities in the lung, brain MRI images to identify abnormalities in the brain, and abdominal CT scans to identify abnormalities in the digestive system.

As used herein, the term weakly labeled means a label assigned to the anatomical image as a whole. No localization of abnormality is provided, for example, the abnormality within the anatomical image is not annotated. The weak label may be indirectly associated with the anatomical image, for example, obtained from an electronic medical record (EMR) of the patient (e.g., from a diagnosis field, and/or BI-RADS score value field) and/or extracted (e.g., using optical character recognition methods of a scanned report, and/or from an analysis of a digital report) from a radiologist report by a human radiologist that interpreted the anatomical image. The weak label provides a global indication whether an indication of abnormality appears somewhere within the anatomical image without specifying the location of the indication of abnormality.

An aspect of some embodiments of the present invention relates to systems, an apparatus, methods, and/or code instructions (stored in a data storage device and executable by hardware processor(s)) for training a deep convolutional neural network (CNN) for detecting an indication of likelihood of abnormality for a target anatomical image based on anatomical training images each associated with an annotation for a whole respective training image, without an indication of a location of the abnormality within the respective anatomical image. Each of the anatomical training images is decomposed into patches. A feature representation (e.g., feature vector) is computed for each patch. A probability that the respective patch includes an indication of abnormality is computed according to the feature representation corresponding to the patch. The probability that the whole anatomical image includes an indication of abnormality is set according to the highest probability value of one of the patches. The deep CNN is trained for detecting an indication of likelihood of abnormality for a target anatomical image according to the patches of the training anatomical training images, the one patch with highest probability identified for each training anatomical image, and the probability set for each respective anatomical training image (according to the one patch).

Optionally, the patches are processed according to the original full resolution of the respective image. No downsizing of the patches relative to the original full resolution image is necessarily required.

The trained deep CNN outputs an indication of likelihood of abnormality. The indication of likelihood of abnormality may be represented as a probability value, and/or as a classification category, optionally a binary classification category. For example, the output may include one of the following classification categories: abnormality, or no-abnormality. It is noted that the classification category of abnormality includes malignancy and may include benign masses. In another example, the output includes one of the following classification categories: malignant lesion, benign lesion, and normal tissue. In yet another example, the output includes a score according to a scoring scale of a certain cancer, for example, a BI-RADS (Breast Imaging-Reporting and Data System) score, or a classification based on one or more BI-RADS scores. BI-RADS is designed as a quality assurance tool by the American College of Radiology (ACR), to make the reporting of breast imaging results more standardized and comprehensible to the non-radiologist reading the report. For example, the malignancy category represents BI-RADS values of 4 and 5, and the no-malignancy category represents BI-RADS values of 1 and 2. The category of BI-RADS value of 3 may be outputted as an independent category indicative of uncertainty. Alternatively, in another example, the BI-RADS score is outputted. It is noted that the neural network may output a probability of the accuracy of the classification.

The deep CNN is trained according to a loss function that considers the single patch most probably indicative of abnormality. Other patches with lower probability values than the one patch with highest probability are excluded and/or ignored. The single patch with highest probability is back propagated through the deep CNN for updating of the coefficients of the deep CNN.

Optionally, the trained deep CNN includes a first stage including a pretrained CNN. The trained deep CNN coefficients are extracted from a last hidden layer of the pretrained CNN. A second stage of the trained deep CNN includes a refined fully connected neural network. The refined fully connected neural network may include three fully connected layers trained from scratch according to the loss function that considers the single patch with highest probability, and back propagates the single patch through the refined fully connected neural network.

An aspect of some embodiments of the present invention relates to systems, an apparatus, methods, and/or code instructions (stored in a data storage device and executable by hardware processor(s)) for detecting an indication of likelihood of abnormality for a target anatomical image by a deep CNN trained based on anatomical training images each associated with an annotation for a whole respective training image without an indication of a location of the abnormality within the respective anatomical image. The target anatomical image is decomposed into patches. A feature representation of each patch is computed by the deep CNN. A probability that the respective patch includes an indication of abnormality is computing by the deep CNN according to the feature representation of the respective patch. A probability indicative of likelihood of abnormality for the target anatomical image is set according to the maximal probability value computed for the one patch with highest probability.

Optionally, an indication of a location indicative of likelihood of abnormality with the anatomical image is provided. The location within the anatomical image is determined according to the corresponding location of one or more patches with highest probability value.

Some implementations of the systems and/or methods and/or apparatus and/or code instructions described herein address the technical problem of training a deep CNN to detect an indication of abnormality in a target anatomical image according to a set of weakly labeled anatomical images.

In the weakly supervised paradigm described herein, only image-level tags are necessary to train a classifier, as opposed to fully supervised classification and detection, which typically requires exhaustive annotations of the medical images. Such annotation which is commonly performed manually is a source of additional errors, which leads to a reduction in accuracy of the trained classifier. Annotation may be incomplete, resulting in ambiguous lesion margins that create controversial annotations, which may lead to a reduction in accuracy of the trained classifier.

Some implementations of the systems and/or methods and/or apparatus and/or code instructions described herein improve performance of a computing device that trains the deep CNN based on the weakly labeled set of anatomical images. The improvement in performance may be based on an increase in accuracy of detecting the indication of abnormality using existing computing resources (e.g., processor(s), and/or data storage), and/or improving the efficiency of detecting the indication of abnormality by a reduction in processing time, a reduction in processor utilization, and/or a reduction in data storage requirements. As described in additional detail in the Examples section below, the systems, method, apparatus, and/or code instructions described herein yields a high performance in terms of AUC, comparing several other methods in the literature Some implementations of the systems and/or methods and/or apparatus and/or code instructions described herein may train the deep convolutional neural network to perform the classification of the anatomical image using high accuracy, using a weakly labeled training set. The systems, methods, apparatus, and/or code instructions described herein may utilize previously obtained anatomical images and radiology interpretation reports to train the deep CNN, without requiring manual annotation by an expert. It is noted that such manual annotation may be unavailable, difficult to obtain, and/or costly to obtain. The accuracy of the deep CNN may be improved by utilizing relatively larger number of anatomical images as training images, without incurring the costs associated with manual annotation. For example, anatomical images and associated whole image annotation may be extracted from existing databases, for example, from a PACS server and/or EMR server.

The deep CNN is trained relatively quickly to provide the location of the identified indication of abnormality, since training a localizer to perform the localization is not explicitly performed. Localization is acquired automatically as a by-product, according to the location within the anatomical image of the patch having highest probability indicative of abnormality.

In another example, the trained deep CNN that is applied to classify a anatomical image performs the classification within a relatively short processing time, using relatively fewer processing resources, and/or using relatively smaller data storage requirements. The improvement in performance may include training the deep CNN and/or applying the deep CNN using less memory, and/or using fewer computational resources (e.g., processor(s) utilization), and/or faster computation time, without sacrificing the accuracy (and in many cases improving the accuracy) of the identifying of abnormality within the image.

The exemplary architecture of the trained CNN described herein improves computational efficiency of the computing device training the deep CNN, for example in terms of reduced processing time, reduced utilization of computational resources, and/or reduced data storage requirements. The improvement in computational efficiency arises, for example, since the patch feature vectors are computed only a single time during a training round by the first stage of the deep CNN, and/or since the second stage includes a small number (e.g., 3 or other value, such as 4, or 4) of fully connected layers.

Some implementations of the systems, methods, apparatus, and/or code instructions described herein do not simply perform automation of a manual procedure, but perform additional automated features which cannot be performed manually by a human using pencil and/or paper. The deep CNN described herein automatically extracts features from the decomposed patches described herein to compute the classification result, which is an entirely different process than that performed by a human interpreter.

The deep CNN described herein may be trained automatically without necessarily requiring human intervention, as no handcrafted features are needed (features are automatically computed and extracted), and no manual annotation of the location of the abnormality within the anatomical image is required (the whole image indication may be automatically extracted from the medical record and/or associated radiology report).

The decomposition of the image into patches allows processing the high resolution image without scarifying the original resolution. Some implementations of the systems and/or methods and/or apparatus and/or code instructions described herein are insensitive to the image size and/or to the number of patches extracted from the image. There is no requirement to wrap the image to a fixed size (as performed by some other methods) which causes the distortion of the image and/or distortion of the lesion. The patch based approach described by some implementations of the systems and/or methods and/or apparatus and/or code instructions described herein allows processing of non-rectangular regions in the image by masking of certain areas, by excluding patches. A combined pre-trained CNN according to some implementations of the systems and/or methods and/or apparatus and/or code instructions described herein allows training on small data sets while shortening the training duration, since only the fully connected layers are trained.

Some implementations of the systems and/or methods and/or apparatus and/or code instructions described herein improve an underling technical process within the technical field of medical image processing, in particular, within the field of automatic analysis of anatomical images to identify indications of cancer.

Some implementations of the systems and/or methods and/or apparatus and/or code instructions described herein provide a unique, particular, and advanced technique of analyzing a target anatomical image by a neural network trained according to a weakly labeled set of anatomical images. The systems and/or methods described herein provide a unique, particular, and advanced technique of creating the trained neural network according to the weakly labeled set of anatomical images, to identify the presence of abnormality within the target anatomical image.

Some implementations of the systems, apparatus, methods and/or code instructions (stored in a storage device executed by hardware processor(s)) described herein generate new data in the form of the neural network trained according to weakly labeled anatomical images.

Some implementations of the systems and/or methods and/or apparatus and/or code instructions described herein are tied to physical real-life components, for example, x-ray machines, MRI machines, and/or ultrasound machines that generate the anatomical image, and computational hardware (e.g., processors, physical memory devices) that analyze the anatomical image.

Accordingly, the systems and/or methods and/or apparatus and/or code instructions described herein are inextricably tied to computer technology and/or physical components (e.g., mammogram machine, processor(s), storage device (s)) to overcome an actual technical problem arising in processing and/or analysis of anatomical images.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A broad variety of traditional machine learning classifiers have been developed for automatic diagnosis of breast cancer, for example, as described with reference to Fernando Soares Servulo de Oliveira, Antonio Oseas de Carvalho Filho, Aristofanes Correa Silva, Anselmo Cardoso de Paiva, and Marcelo Gattass. *Classification of breast regions as mass and non-mass based on digital mammograms using taxonomic indexes and svm. Computers in biology and medicine,* 57:42-53, 2015, Chun-Chu Jen and Shyr-Shen Yu. *Automatic detection of abnormal mammograms in mammographic images. Expert Systems with Applications,* 42(6): 3048-3055, 2015. However, such methods require defining handcrafted discriminative features.

Other methods have explored deep learning approaches to address the automatic classification of lesions in mammography, for example, as described with reference to Dan C Ciresan, Alessandro Giusti, Luca M Gambardella, and Jurgen Schmidhuber. *Mitosis detection in breast cancer histology images with deep neural networks. In International Conference on Medical Image Computing and Computer-assisted Intervention,* pages 411-418. Springer, 2013. 7. Kersten Petersen, Mads Nielsen, Pengfei Diao, Nico Karssemeijer, and Martin Lillholm. *Breast tissue segmentation and mammographic risk scoring using deep learning. In International Workshop on Digital Mammography,* pages 88-94. Springer, 2014., Michiel Kallenberg, Kersten Petersen, Mads Nielsen, Andrew Y Ng, Pengfei Diao, Christian Igel, Celine M Vachon, Katharina Holland, Rikke Rass Winkel, Nico Karssemeijer, et al. *Unsupervised deep learning applied to breast density segmentation and mammographic risk scoring. IEEE transactions on medical imaging,* 35(5): 1322-1331, 2016. However, such other methods require the expensive process of annotating images, which poses a significant bottleneck in supervised learning for medical imaging. Such detailed annotations are rarely available in practice.

Deep learning based algorithms are increasing being utilized in complicated pattern recognition problems, especially in big data domain, for example, as described with reference to K. Simonyan and A. Zisserman. *Very deep convolutional networks for large-scale image recognition. CoRR,* abs/1409.1556, 2014. The deep architecture may be used to discover latent representation efficiently and ultimately to enhance detection and classification accuracy. However, such application of deep learning methods are generally applied to natural images, in contrast to the systems, methods, apparatus, and/or code instructions described herein that are applied to anatomical images.

Multiple Instance Learning (MIL) based methods are a variation of supervised learning for problems having global labels, namely at the whole image level. By representing an image as a bag of multiple instances, classification may be made by considering the predicted bag ingredient labels instead of the traditional global image features, for example, as described with reference to Thomas G Dietterich, Richard H Lathrop, and Tomas Lozano-Perez. *Solving the multiple instance problem with axis-parallel rectangles. Artificial intelligence,* 89(1):31-71, 1997, Oded Maron and Tomas Lozano-Perez. *A framework for multiple-instance learning. Advances in neural information processing systems,* pages 570-576, 1998. While such use cases are frequently found in medical image analysis, the amount of research is limited, particularly in mammography diagnosis, for example, as described with reference to Gwenole Quellec, Mathieu Lamard, Michel Cozic, Gouenou Coatrieux, and Guy Cazuguel. *Multiple-instance learning for anomaly detection in digital mammography. IEEE transactions on medical imaging,* 35(7): 1604-1614, 2016. Some recent studies applying MIL combined with deep learning for weakly supervised classification tasks are performed for natural images which are different than medical images, include for example, Jiajun Wu, Yinan Yu, Chang Huang, and Kai Yu. *Deep multiple instance learning for image classification and autoannotation.* Other studies based on MIL tackle the problem of recognition of larger anatomical structure in CT scans using different architectures, for example, In 2015 *IEEE Conference on Computer Vision and Pattern Recognition (CVPR),* pages 3460-3469. IEEE, 2015., Zhennan Yan, Yiqiang Zhan, Zhigang Peng, Shu Liao, Yoshihisa Shinagawa, Shaoting Zhang, Dimitris N Metaxas, and Xiang Sean Zhou. *Multi-instance deep learning: Discover discriminative local anatomies for bodypart recognition. IEEE transactions on medical imaging,* 35(5):1332-1343, 2016. Yan et al. use a cascade classifier and focus on background classification (referred to as non-informative patches). The patches are extracted from CT slices and used to boost learning for recognition of larger body parts appearing in the slice images.

Other studies address the problem of mammogram classification from weakly labeled sets using MIL by different approaches. For example, ZHU W, LOU Q., VANG Y. S., XIE X.: *Deep multi-instance networks with sparse label assignment for whole mammogram classification In arXiv* (2016) assume that lesions occupy a small portion of the whole mammogram. A sparsity constraint is added in the loss function enforcing the probability distribution of patches to be sparse (mostly negative, with zero probability). Zhu et al use the CNN for representation of the whole mammogram and in order to use a pretrained network (on ImageNet) they downsize the large MG images by factor 7-14 on each side to reach 224×224 size. The harsh downsizing action causes a significant loss of information in the mammogram. It is well known that malignant lesions often appear as masses or microcalcifications and can be as small as 50×50 pixels (cf. statistics on INbreast data set in Zhu et al). In contrast, some implementations of the systems, methods, apparatus, and/or code instructions described herein use a patch-based approach with a max-pooling loss function, resulting localization in full resolution.

Figure 2:
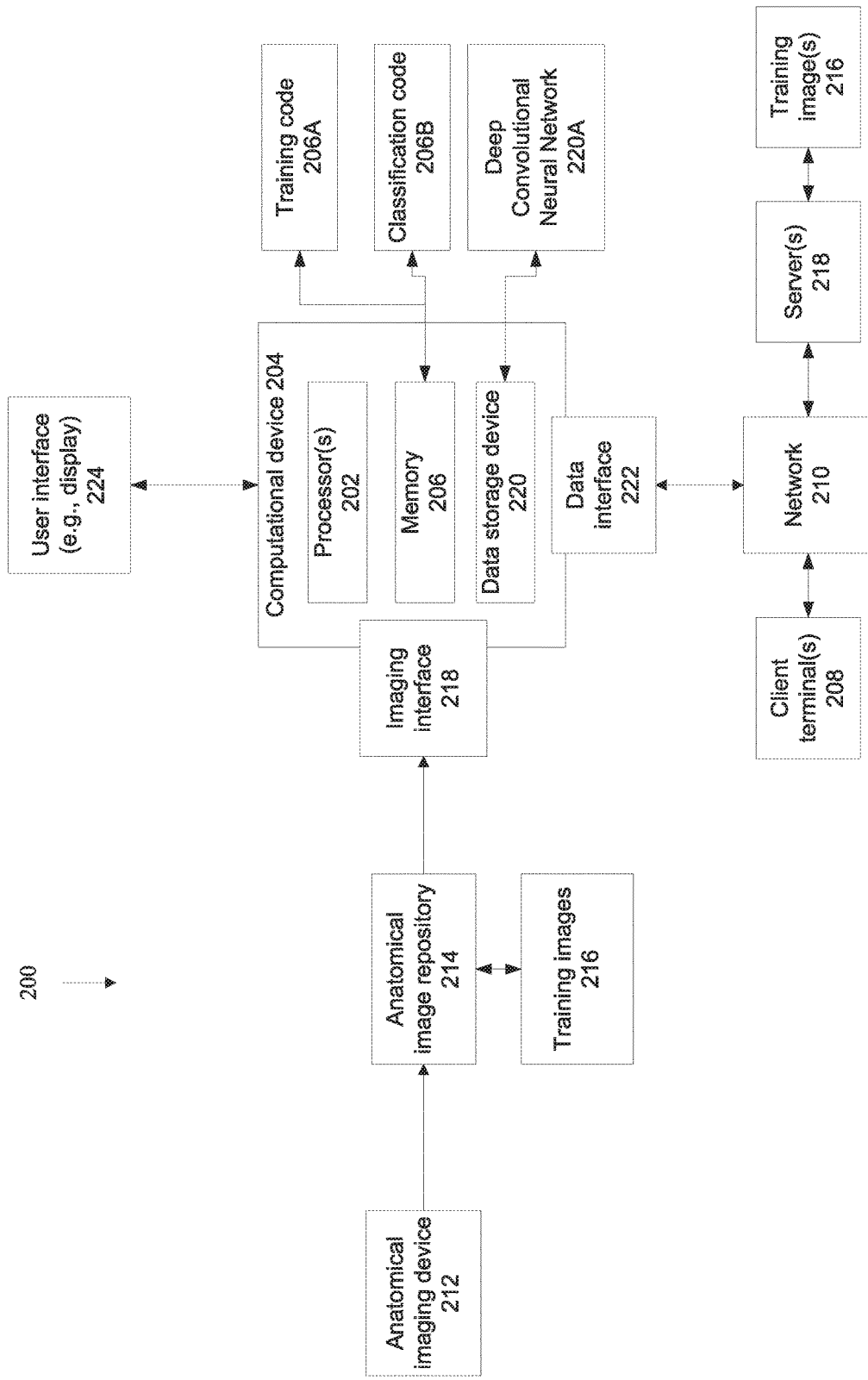
FIG. 2 is a components of a system that trains a deep convolutional neural network according to a weakly labeled set of anatomical training images, in accordance with some embodiments of the present invention.
Figure 3:
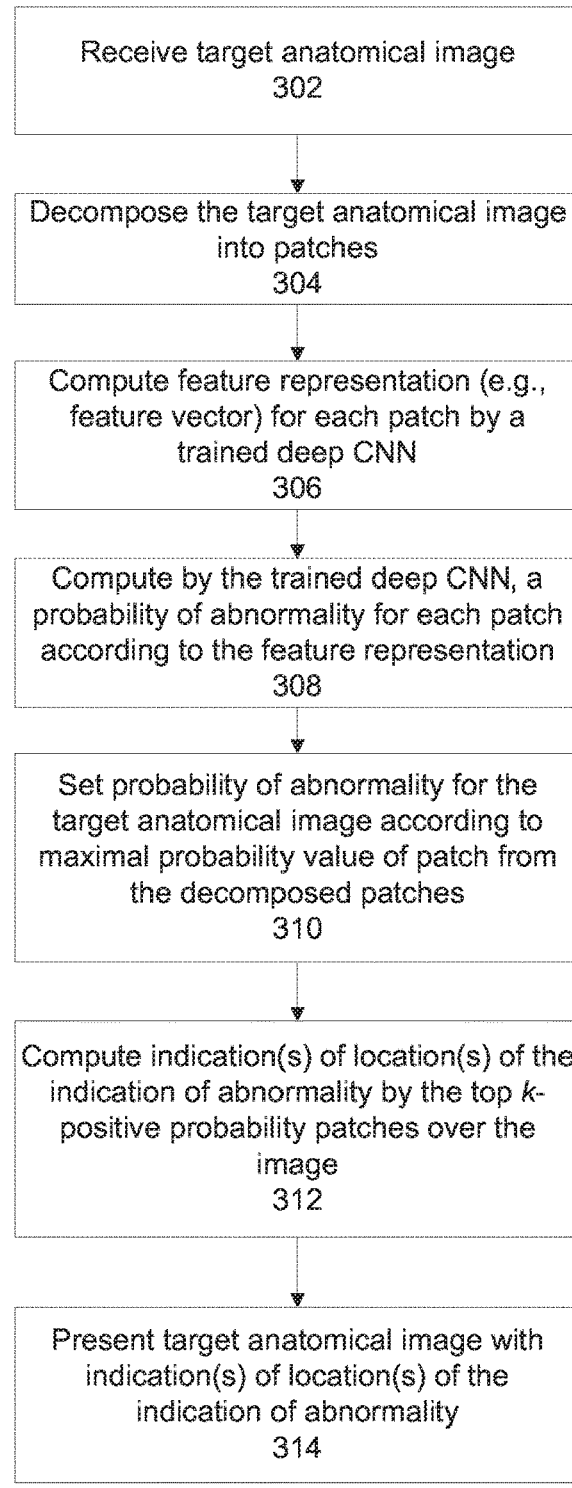
FIG. 3 is a flowchart of a method of computing an indication of abnormality (e.g., malignant or benign) finding for a target anatomical image based on a deep convolutional neural network trained according to a weakly labeled set of anatomical training images, in accordance with some embodiments of the present invention.

Reference is now made to FIG. 1 which is a flowchart of a method for training a deep convolutional neural network according to a weakly labeled set of anatomical training images, in accordance with some embodiments of the present invention. Reference is also made to FIG. 2, which is a block diagram of components of a system 200 that trains a deep convolutional neural network according to a weakly labeled set of anatomical training images, in accordance with some embodiments of the present invention. System 200 may implement the features of the method described with reference to FIG. 1, by one or more hardware processors 202 of a computing device 204 executing code instructions stored in a memory (also referred to as a program store) 206. Reference is also made to FIG. 3, which is a flowchart of a method of computing an indication of abnormality for a target anatomical image based on a deep convolutional neural network trained according to a weakly labeled set of anatomical training images, in accordance with some embodiments of the present invention. Components of system 200 described with reference to FIG. 2 may implement the method of computing the indication of abnormality described with reference to FIG. 3.

Computing device 204 may be implemented as, for example, a client terminal, a server, a radiology workstation, a virtual machine, a virtual server, a computing cloud, a mobile device, a desktop computer, a thin client, a Smartphone, a Tablet computer, a laptop computer, a wearable computer, glasses computer, and a watch computer.

Computing device 204 may include locally stored software that executes one or more of the acts described with reference to FIG. 1 and/or FIG. 3, and/or may act as one or more servers (e.g., network server, web server, a computing cloud) that provides services (e.g., one or more of the acts described with reference to FIG. 1 and/or FIG. 3) to one or more client terminals 208 (e.g., remotely located radiology workstations) over a network 210, for example, providing software as a service (SaaS) to the client terminal(s) 208, providing an application for local download to the client terminal(s) 208, and/or providing functions using a remote access session to the client terminals 208, such as through a web browser.

Computing unit 204 receives 2D anatomical image(s) captured by an anatomical imaging machine(s) 212, for example, a standard two dimensional (2D) anatomical imaging device, a sequence of 2D anatomical images (e.g., captured by a fluoroscopic machine), and/or a three dimensional (3D) anatomical imaging device from which 2D images are optionally extracted as slices (e.g., CT, MRI). Anatomical imaging machine(s) 212 may include a standard x-ray based machine, a CT scanner, an MRI machine, and an ultrasound machine.

Anatomical images captured by anatomical imaging machine 212 may be stored in an anatomical imaging repository 214, for example, a storage server, a computing cloud, a PACS server (picture archiving and communication system), and a hard disk. The anatomical images stored by anatomical imaging repository 214 may include anatomical images of patients for analysis, and/or training images 216 that have been previously analyzed (e.g., by radiologists) and weakly labeled with findings indicative of abnormality.

Exemplary anatomical images include mammographic images, CT scans (e.g., chest CT, abdominal CT), MRI scans, and ultrasound scans.

The anatomical images may be stored in the PACS and/or electronic medical record (EMR) of each patient. The training images 216 may be extracted from the PACS and/or EMR with the radiologist finding. For example, the radiology report may be analyzed to extract the BI-RADS score, and/or the BI-RADS score may be extracted from a value of a field in the EMR.

Training images 216 are used to train the deep convolutional neural network, as described herein. It is noted that training images 216 may be stored by a server 218, accessibly by computing unit 204 over network 210, for example, the PACS and/or EMR server.

Computing device 204 may receive the anatomical image(s) via one or more imaging interfaces 226, for example, a wire connection (e.g., physical port), a wireless connection (e.g., antenna), a network interface card, other physical interface implementations, and/or virtual interfaces (e.g., software interface, application programming interface (API), software development kit (SDK), virtual network connection).

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may store training code 206A that execute one or more acts of the method described with reference to FIG. 1, and/or classification code 206B that execute one or more acts of the method described with reference to FIG. 3.

Computing device 204 may include a data storage device 220 for storing data, for example, a trained deep convolutional neural network 220A trained based on a weakly labeled set of anatomical training images, as described with reference to FIG. 1. Data storage device 220 may be implemented as, for example, a memory, a local hard-drive, a removable storage unit, an optical disk, a storage device, a virtual memory and/or as a remote server 218 and/or computing cloud (e.g., accessed over network 210). It is noted that deep convolutional neural network 220A may be stored in data storage device 220, for example, with executing portions loaded into memory 206 for execution by processor(s) 202.

Computing device 204 may include data interface 222, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download additional training images 216.

Computing device 204 may connect using network 210 (or another communication channel, such as through a direct link (e.g., cable, wireless) and/or indirect link (e.g., via an intermediary computing unit such as a server, and/or via a storage device) with one or more of:

Client terminal(s) 208, for example, when computing device 204 acts as a server providing services (e.g., SaaS) to remote radiology terminals and/or remote medical servers, by analyzing remotely obtained anatomical images for computing the likelihood of abnormality in a tissue portion, for example, one or both breasts.

Server 218, for example, when server 218 is part of picture archiving and communication system (PACS), which may storage large numbers of anatomical images for analysis, for example, captured by a anatomical machine of a radiology clinic.

Anatomical imaging repository 214 (e.g., PACS server, EMR server) that stores anatomical images and associated weak labels (e.g., radiological finding report).

Computing device 204 includes or is in communication with a user interface 224 that includes a mechanism designed for a user to enter data (e.g., patient data, define location of training anatomical images) and/or view the computed indication of abnormality and/or view the patch (es) associated with highest probability of abnormality. Exemplary user interfaces 224 include, for example, one or more of, a touchscreen, a display, a keyboard, a mouse, and voice activated software using speakers and microphone.

Referring now back to FIG. 1, at 102, multiple anatomical training images are obtained. Each anatomical training image including at least one target tissue (e.g., breast) portion in which abnormality may be found, and an associated weak label (also referred to as an annotation) indicative of abnormality for the whole respective anatomical training image. The anatomical training images and/or the associated annotation may be obtained, for example, from a PACS server, and/or an EMR server, for example, by an analysis of the radiology report and/or extraction The training anatomical image may have been obtained as part of a routine cancer screening program, for example, mammograms captured for breast cancer screening.

The weak label is selected according to the desired output of the trained deep CNN. For example, to output a binary classification of abnormality or no abnormality, anatomical training images with BI-RADS scores of 1 and 2 may be tagged as no abnormality, and anatomical training images with BI-RADS scores of 4 and 5 may be tagged as abnormality. Anatomical training images for which the manual radiology interpretation is uncertain (e.g., BI-RADS score of 3) may be ignored and/or excluded from the training set.

The anatomical images may be 2D images, for example, acquired by an x-ray based machine and/or ultrasound machine. Alternatively or additionally, the anatomical images may be 2D images obtained as slices from a 3D image volume, for example, acquired by an MRI and/or CT.

An abnormality appearing in the anatomical training images is not associated with a (optionally manual) annotation indicative of location of the abnormality within the respective anatomical training image.

The size of each of the anatomical training images is arbitrary and/or the size may vary between the anatomical training images.

Optionally, the anatomical training images are pre-processed. Optionally, tissue portion(s) where abnormality may be found (e.g., the breast and/or axilla regions) are segmented from each anatomical image. As used herein, the term anatomical image may refer to the segmented tissue (e.g., breast) portion.

Acts 104-110 are executed for each respective anatomical training image.

At 104, the respective anatomical training image is decomposed into patches. The number of patches is arbitrary and/or the number of patches per anatomical image may vary between anatomical images.

Optionally, the respective anatomical training image is decomposed based on a sliding window moved within the respective anatomical training image to extract each of the patches. The siding window may be moved to cover the entire image. Exemplary number of extracted patches include: about 100×100, or about 224×224, or about 500×500 or other dimensions. The size of each extracted patch is, for example, about 10×10 millimeters (mm), or about 15×15 mm, or about 25×25 mm, or other values.

Optionally, the extracted patches overlap. Each patch may overlap with one or more other patches. The overlap may be, for example, about 10%, or about 25%, or about 50%, or about 70%, or other values.

Optionally, the patches are decomposed from the respective anatomical training image without downsampling and/or in full resolution (i.e., corresponding to the original resolution of the input image). The patches are extracted from the anatomical image, which may be captured at high resolution to allow detection of small size findings, without reducing the resolution of each patch. The resolution of each patch corresponds to the resolution of the anatomical image.

The number of patches may be increased and/or balanced by data augmentation methods. For example, rotation (e.g., 8×45 degrees, or other number or rotation and/or other degrees of rotation), flips, random shifts, and/or different sharpening. The set of anatomical images positive for abnormality may be increased when a limited number of such images are available.

As used herein, the patches decomposed from the anatomical training is sometimes referred to herein as a bag.

In terms of mathematical representation, the set of training anatomical images mathematically denoted as A include pairs of bags and associated labels mathematically denoted as $$\{(X_i, Y_i)\}_{i=1}^{N}, \text{ where } X_i = \{x_{ij}\}_{j=1}^{m_i},$$

wherein $X_i$ denotes the bag representing the whole i-th anatomical image along with the associated label denoted $Y_i$, and $x_{ij}$ denotes the j-th patch of the i-th anatomical image. To obtain a binary classification, the bag is labeled positive when at least one patch in the bag is positive (i.e., includes an indication of likelihood of abnormality). A bag is labeled negative when all the patches in the bag are negative (i.e., none of the patches include an indication of likelihood of abnormality). It is noted that none of the individual patches are associated with their own label. The patches of the bag as associated with a global label assigned to the bag as a whole. The systems, methods, apparatus, and/or code instructions described herein classify previously unseen bags and/or patches based on the deep convolutional neural network trained on labeled bags. It is assumed that patch labels may exist for each patch, where such individual patch labels are denoted $y_{ij} \in \{y_+, y_-\}$, however such individual patch labels are not known during training of the deep CNN. The assumption for the label of the anatomical training image may be mathematically represented as:

$$Y_i = \max_j(y_{ij})$$

It is noted that training the deep CNN is performed differently in comparison to training a classical classifier to perform a classical binary classification task. For example, in traditional supervised learning, the training data is provided as pairs, mathematically represented as $\{(x_i,y_i)\}_{i=1}^{N}$, where $x_i$ denotes the input image or features, and the normal vs abnormality (e.g., including benign and/or malignant) class label of $x_i$ is denoted $y_i \in \{y_+, y_-\}$. Classical supervised learning methods train a classical classifier, mathematically represented as $h:x \rightarrow y$, that will accurately predict a label y for a new image x. It is noted that such classical classifiers are unsuitable for classification of anatomical images, since classical classifiers perform a global image analysis, while anatomical images are determined to be malignant or not based on small localized indications of abnormality.

At 106, a feature representation is computed for each patch. The feature representation may be implemented as a feature vector. The number of features extracted for each patch may be, for example, 4096, or other values.

Optionally, the features are extracted by the trained CNN of the first stage of the deep CNN, as described herein.

At 108, a probability that the respective patch includes an indication of abnormality is computed according to the feature representation of the respective patch. Optionally, the probability is computed by the refilled fully connected neural network of a second stage of the deep CNN, as described herein.

Optionally, the probability comprises a probabilistic geometric prior value denoting areas on a border of the tissue (e.g., breast) portion appearing in the patch, as described with reference to act 112. The probability including the probabilistic geometric prior value denoting areas on the border of the tissue (e.g., breast) portion of the patch is provided as input into a loss function, as described with reference to act 112.

At 110, a probability indicative of likelihood of abnormality for the respective anatomical image is set according to the maximal probability value computed for the patches. The patch having maximal probability value is identified from the patches extracted from the respective anatomical image. The probability of the anatomical image is defined according to the maximal probability of the identified patch. Patches associated with lower probability values may be ignored.

At 112, a deep convolutional neural network is trained for detecting an indication of likelihood of abnormality for a target anatomical image according to the patches of the anatomical training images, the identified patch with highest probability value, and the probability of each respective anatomical training image.

The deep convolutional neural network is trained according to a loss function. It is noted that the cross entropy loss function, which is used to train a classical classifier to perform binary classification by discrimination between classes, is unsuitable for training the deep CNN according to the patches of weakly labeled anatomical images. The cross entropy loss function is unsuitable since negative patches (i.e., patches that do not include an indication of abnormality) are present in positive images (i.e., an anatomical image labeled as indicative of abnormality without specifying where the abnormality is located within the anatomical image). Since such negative patches would obtain high probabilities even for positive anatomical images, as no separation between the two classes may be obtained.

The loss function computes a log likelihood loss according to a probability that a certain patch of the patches of the respective anatomical image is classified as indicative of abnormality based on coefficients of the deep CNN.

The loss function considers one patch, the patch with the highest probability, as most probably indicative of abnormality. The one patch represents the most discriminative patch of the anatomical image. Other patches with lower probability are not considered. The one patch is back propagated through the deep CNN for updating the coefficients of the deep CNN.

An exemplary loss function is mathematically represented as:

$$\mathcal{L}(\theta) = \sum_{\substack{X_i \in \Lambda \\ Y_i = y_+}} \log\left(\max_{x_{ij} \in X_i} \mathbb{P}(y_+ | x_{ij}, \theta)\right) + \sum_{\substack{X_i \in \Lambda \\ Y_i = y_-}} \log\left(1 - \max_{x_{ij} \in X_i} (\mathbb{P}(y_+ | x_{ij}, \theta))\right)$$

Where:

$x_{ij}$ denotes the respective patch of the respective anatomical image, $\theta$ denotes CNN coefficients, and $\mathbb{P}(y_+|x_{ij},\theta)$ denotes the probability that the local patch denoted $x_{ji}$ is classified as positive based on the CNN coefficients $\theta$.

Optionally, the probability including the probabilistic geometric prior value denoting areas on the border of the tissue (e.g., breast) portion of the patch (as described with reference to act 108) is mathematically represented as:

$$\omega(x_{ij}) \mathbb{P}(y_+|x_{ij},\theta)$$

where:

$\omega(x_{ij})$ denotes the probabilistic geometric prior, for example, the presence of skin and/or axilla regions.

There may be certain regions in the image that are irrelevant to detection of abnormalities, since the abnormalities being searched for cannot be found in such regions, for example, regions outside of the body, and/or issues outside of the target tissue (e.g., skin and/or pectoral muscles when searching for abnormalities in a breast). To prevent classification errors from such irrelevant regions bordering the relevant tissue (e.g., breast), the distance from such edges may be computed. The distance from the edges may be mathematically represented as:

$$\omega(x_{ij}) = 1 - \frac{\mathcal{A}(x_{ij} \cap \mathcal{B})}{\mathcal{A}(x_{ij})}$$

where:

$\mathcal{A}(x_{ij})$ denotes the area of patch $x_{ij}$ and $\mathcal{B}$ denotes the bordering problematic regions (e.g., axilla, skin).

Patches intersecting the target tissue (e.g., breast) outline may be excluded. When the images include the breast, including patches depicting the pectoral muscle resulted in inferior performance particularly due to existence of lymph nodes having a similar appearance as abnormal masses. Patches that included pectoral muscle may be excluded. It is noted that relevant target tissue (e.g., breast) close to the excluded regions are still considered due to the overlapped patches.

Optionally, a binary weight implementation is applied. The weight and/or masking provides for processing of non-rectangular regions. The binary weights may be mathematically represented as:

$$\omega(x_{ij}) = \begin{cases} 1, & x_{ij} \cap \boxtimes = \emptyset \\ 0, & x_{ij} \cap \boxtimes \neq \emptyset \end{cases}$$

The target tissue (e.g., breast) contour may be segmented, for example, using a global object preserving threshold, and the nearby irrelevant tissue (e.g., pectoral muscle) may be segmented, for example, by a dynamic programming of connected points of high gradient.

The loss function is not necessarily differentiable. A surrogate function may be used by first sorting the patches according to respective scores (e.g., positive probability), then selecting the patch with the maximum score for input to a standard cross entropy function. The selected patch, denoting the most discriminative patch, represents the whole image and is used for back propagation and update of the coefficients (denoted θ).

At 114, the trained deep CNN is provided for classification of a new target anatomical image. The deep CNN may be stored and/or executed by the computing device described herein.

An exemplary architecture of the trained deep CNN is now described. The exemplary trained deep CNN includes a first and second stage. The first stage includes a pretrained CNN. Training of the first stage (e.g., VGG) may be fixed, such that the CNN weights are frozen and not updated during the training. The trained deep CNN coefficients are extracted from a last hidden layer of the pretrained CNN. The feature representation of the patches is based on the coefficients extracted from the last hidden layer of the pretrained CNN. The convolutional neural network coefficients extracted from the last hidden layer of the first stage are computed once for each patch. Fixing of the first stage allows the patch feature vectors to be computed only once, prior to training, significantly reducing the computation cost, for example, when the second stage (e.g., the refining network) includes only three fully connected layers.

The second stage includes a refined fully connected neural network. The refined fully connected neural network may include three (or other small number, for example, 4 or 5, to maintain computational efficiency) fully connected layers trained from scratch according to the loss function described herein that considers one patch with highest probability value and back propagates the one patch through the refined fully connected neural network. The refined fully connected neural network computes the probability that the respective patch includes an indication of abnormality according to the corresponding feature vector. The three fully connected layers of the refined fully connected neural network may include rectified linear units (ReLUs) as non-linear layers. The second stage may be optimized using momentum stochastic gradient descent, for example, according to a stochastic gradient descent solver with a mini-batch size of 70-256 varied according to the data set (without batch normalization).

An exemplary a dynamic learning rate includes $[0.5, 3.5] \times 10^{-3}$, an exemplary momentum include 0.9 and exemplary weight decay includes $10^{-3}$ and $10^{-4}$ for two different data sets (it is noted that values other than the exemplary values described may be used). An exemplary stopping criterion includes 20-30 epochs according to a validation set. The results may be post-processed using a number (e.g., 15 or other value) of augmentations on the test patches as described herein, then averaging over the top number K (e.g., =4) patch probability scores to reach the image level probability. The post-processing improves outlier rejection and/or reduce false positives.

Figure 4:
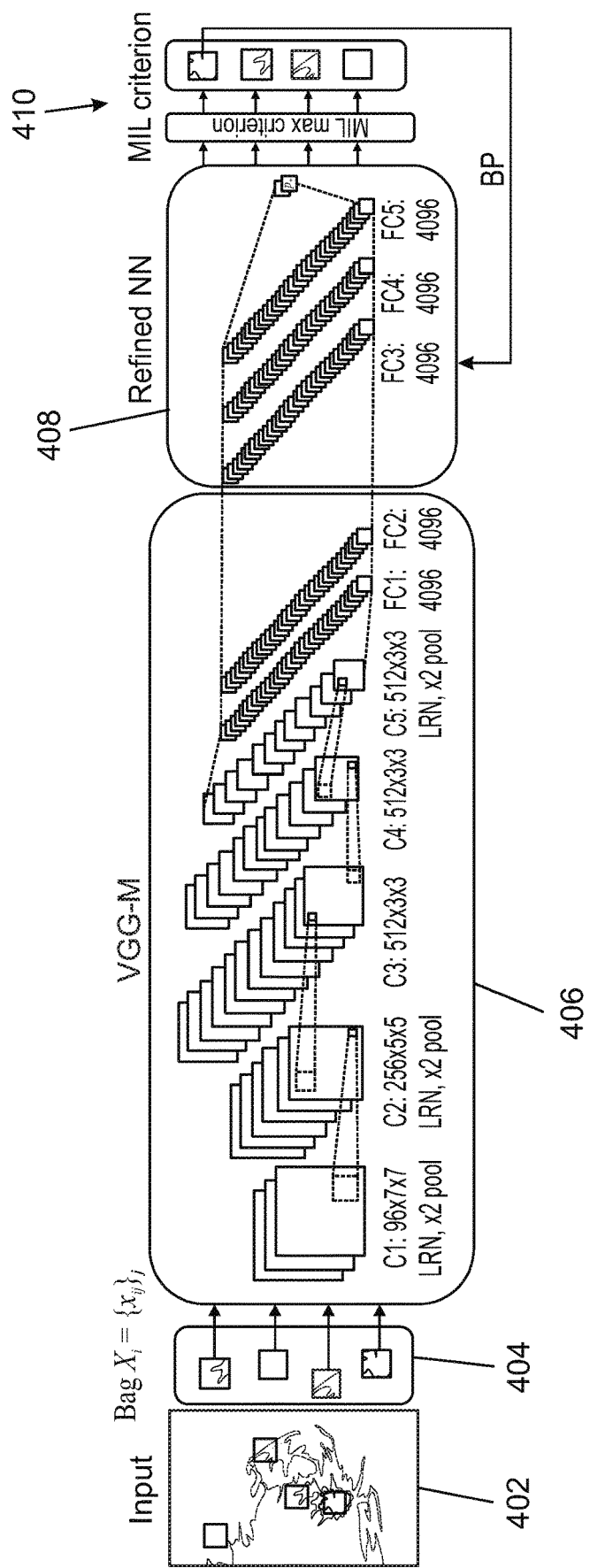
FIG. 4 is a depicting an exemplary architecture of the deep CNN trained based on a training set of weakly labeled anatomical images, in accordance with some embodiments of the present invention.

Reference is now made to FIG. 4, which is a schematic depicting an exemplary architecture of the deep CNN trained based on a training set of weakly labeled anatomical images, in accordance with some embodiments of the present invention.

At 402, a anatomical image is received as input, for example, as described with reference to act 102 and/or 302.

At 404, the anatomical image is decomposed into patches to create a bag, for example, as described with reference to act 104 and/or 304.

At 406, each image patch is processed by a pertained network that outputs a 4096D feature vector. The pretrained network represents the first stage described herein. Optionally, a transfer learning approach is implemented by using the pretrained network, for example, the VGG-M network as described with reference to K. Chatfeld, K Simonyan, A. Vedaldi, and A. Zisserman. *Return of the devil in the details: Delving deep into convolutional nets. In British Machine Vision Conference*, 2014. The VGG-M network may be trained on an existing dataset, for example, the imageNet dataset. The CNN coefficients may be extracted from the last hidden layer as the 4096D feature vector.

It is noted that the first stage, for example, implemented as VGG-M, is fixed, such that the patch feature vectors are computed a single time during a training round.

At 408, the refined fully connected neural network associates a class score to each feature vector (i.e., associated with a certain patch). Optionally, the refined fully connected neural network includes three fully connected layers. Optionally, the refined fully connected neural network is trained from scratch according to the loss function described herein. Optionally, rectified linear units (ReLUs) are used as nonlinear layers in the refined fully connected neural network.

At 410, the probabilities computed for the patches are aggregated into a final probability for the whole image (i.e., for the bag, for the patches of the anatomical image).

The trained deep CNN classifies the anatomical image according to the most probably positive patch.

Referring now to FIG. 3, at 302, the target anatomical image is obtained.

At 304, the target anatomical training image is decomposed into patches, for example, as described with reference to act 104 of FIG. 1.

At 306, a feature representation of each patch is computed by the trained deep convolutional neural network, for example, as described with reference to act 106 of FIG. 1.

At 308, a probability that the respective patch includes an indication of abnormality is computed by the trained deep CNN according to the feature representation of the respective patch, for example, as described with reference to act 108 of FIG. 1.

At 310, a probability indicative of likelihood of abnormality is set for the target anatomical image according to the maximal probability value computed for the patches, for example, as described with reference to act 110 of FIG. 1.

At 312, an indication of a location indicative of likelihood of abnormality is identified according to the corresponding location with the target anatomical image of one or more patches associated with the maximal probability value. For example, the top 3-5 patches in descending order of probability value are selected and their corresponding locations within the target anatomical image is determined.

Optionally, the patches are scored according to the computed likelihood of abnormality (e.g., positive probability). The most highly scored patch(es) represent the discriminative regions in the image and indicate the location of the abnormalities. The localization provides an efficient mechanism for presentation of the analysis of the results and/or helps the user in understanding the outcome. Note that the localization is obtained without having any local labels in the training set.

At 314, the target anatomical is provided for presentation on a display (e.g., of a client terminal) with one or more overlay markings. Each marking is indicative of the location of one of the highest probability patches within the anatomical image.

The location of the malignancy within the anatomical image is obtained according to the location(s) of the patch (es) within the anatomical image. For example, the top three (or other number) of patches associated with decreasing probabilities, staring from the highest probability value as selected. The regions on the anatomical image corresponding to the top three patches may be marked, for example, with a border indicating the border of the patch. The patches may be color coded to indicate their relative rank, for example, green is the patch with highest probability, red is the patch with second highest probability, and blue is the patch with third highest probability.

Alternatively or additionally, the indication of likelihood of malignancy (e.g., malignant, or not malignant) is stored in association with the stored anatomical image (e.g., in the PACS server and/or in the EMR server), and/or is presented on a display, and/or transmitted to another device (e.g., as a pop-up message, email, and/or short message presented on a mobile phone).

Various embodiments and aspects of the present invention as delineated hereinabove and as claimed in the claims section below find calculated support in the following examples.

EXAMPLES

Reference is now made to the following examples, which together with the above descriptions illustrate some embodiments of the invention in a non limiting fashion.

Inventors performed a computational evaluation according to the systems and/or methods and/or apparatus and/or code instructions described herein, for example, with reference to FIGS. 1-3, to evaluate an indication of likelihood of abnormality for a target anatomical image, in particular a target mammographic image, based on a deep convolutional neural network trained according to a weakly labeled set of anatomical training images, in particular, a weakly labeled set of mammographic training images.

A first evaluation was conducted based on a data set of mammographic images collected at a large multi-center hospital, referred to herein as IMG. The data set includes 2,234 full-filed digital mammograms (FFDM) from a BI-RADS distribution of 1345, 689 and 53, 147 corresponding to findings in the image associated with BI-RADS 1, 2 and 4, 5 respectively. Images with BI-RADS 3 were removed from the test set to decrease the chance for inter-observer variability. The mammograms include various findings such as masses, macro and micro calcifications.

Mammograms were pre-processed to include one of two labels, BI-RADS 4, 5 as positive (76 cases) and BI-RADS 1, 2, 3 as negative (687 cases). All types of suspiciously malignant abnormalities were included into the positive class to distinguish between any severe abnormality from normal images (BI-RADS:1) and most likely benign findings (BI-RADS:2). This data split raises a technical challenge as the trained deep convolutional neural network has to discriminate between mammographic images with similar types of findings, for example, malignant versus benign masses or different types of micro-calcifications (MCC), often ambiguous even for expert radiologists.

A second evaluation was performed based on mammographic images available from the INbreast publicly available FFDM data set Ines C Moreira, Igor Amaral, Ines Domingues, Antonio Cardoso, Maria Joao Cardoso, and Jaime S Cardoso. *Inbreast: toward a full-field digital mammographic database. Academic radiology,* 19(2):236-248, 2012. The INbreast is a relatively small data set including 410 mammograms from 115 cases. The same split of images according to BI-RADS score described with reference to the first evaluation was performed on the INbreast images, which provided 90 positive and 300 negative mammograms.

The performance assessment was carried out with 5 fold patient-wise cross-validation. At each train and test iteration, all the images from the patient under test were strictly excluded from the training set, to avoid data contamination and over-fitting.

The results of the evaluations are summarized in Table 1, which presents binary classification performance measured by AUC for different methods with the associated testbed. Methods are differentiated by the type of annotation (weak vs. full annotation), source, and size (# of images) of the data set. Note the high AUC value obtained by the systems, method, apparatus, and/or code instructions described herein for the IMG dataset set with a sufficiency large number of images.

TABLE 1

| Methodology | Labels | Data set | Type | # Images | AUC |
| --- | --- | --- | --- | --- | --- |
| Self-TL | Weak | MIAS | Scanned | 322 | 0.675 |
| Deep Features | Full Annotation | INbreast | FFDM | 116 | 0.760 |
| As described herein | Weak | IMG | FFDM | 2,034 | 0.851 |
| As described herein | Weak | INbreast | FFDM | 390 | 0.689 |

The area under the ROC curve (AUC) measure was used for performance assessment due to the high imbalance distribution between positive (BI-RADS 4, 5) and negative (BI-RADS 1, 2) classes in the data sets (only 9% of mammograms in the IMG set are positive). The trained deep convolutions neural network described herein produced an average AUC of 0.851+/−0.04 on the IMG data set, without requiring the annotation of any finding in the mammographic images. It is noted that testing on the small INbreast data set resulted in a lower AUC of 0.689+/−0.064. The high standard deviation in the Inbreast results reflects the influence of the data size, in terms of learning capability and/or statistical validity of the results.

Further analysis shows that on average, 30% of the false positives are from BI-RADS 2 category. The false positive results indicate that many network errors may be associated with wrong classification of masses and calcifications, which often pose a challenge even for expert radiologists.

Some implementations of the systems, methods, apparatus, and/or code instructions described herein (referred to as 'as described herein' in Table 1) were compared to the Self-Transfer Learning method (Self-TL) as described with reference to Sangheum Hwang and Hyo-Eun Kim. *Self-* transfer learning for weakly supervised lesion localization. In International Conference on Medical Image Computing and Computer-Assisted Intervention, pages 239-246. Springer, 2016, and to the Deep-Features method as described with reference to Neeraj Dhungel, Gustavo Carneiro, and Andrew P Bradley. *The automated learning of deep features for breast mass classification from mammograms. In International Conference on Medical Image Computing and Computer-Assisted Intervention*, pages 106-114. Springer, 2016. It is noted that the Self-TL method is based on weakly labeled data sets, using a CNN, divided into two branches, one for classification and the other for detection. The network works on downsized images (500×500) with low resolution in localization, and strongly impacting the low classification performance reaching 0.675 ROC-Area Under the Curve, with results reported on digitally scanned images. The Deep-Features method is based on a fully annotated data set. The Deep-Feature method adopts the traditional approach where the images are categorized based on detection and classification of the masses in the mammograms. Although the performance indexes quoted provide a subjective evaluation due to different data sets and splits, the results demonstrate the high capability of the systems, methods, apparatus, and/or code instructions described herein to successfully categorize severe cases in mammography. The systems, methods, apparatus, and/or code instructions described herein significantly outperform the weak supervision method of Self-TL that results in AUC of 0.675. A significantly higher AUC was obtained with respect to the Deep-Features method, which results in AUC of 0.760, despite using a fully-annotated data set, and only considering masses as abnormalities. Note that the systems, methods, apparatus, and/or code instructions described herein are further capable of distinguishing between different types of abnormalities such as micro-calcifications which may appear in both classes.

Figure 5:
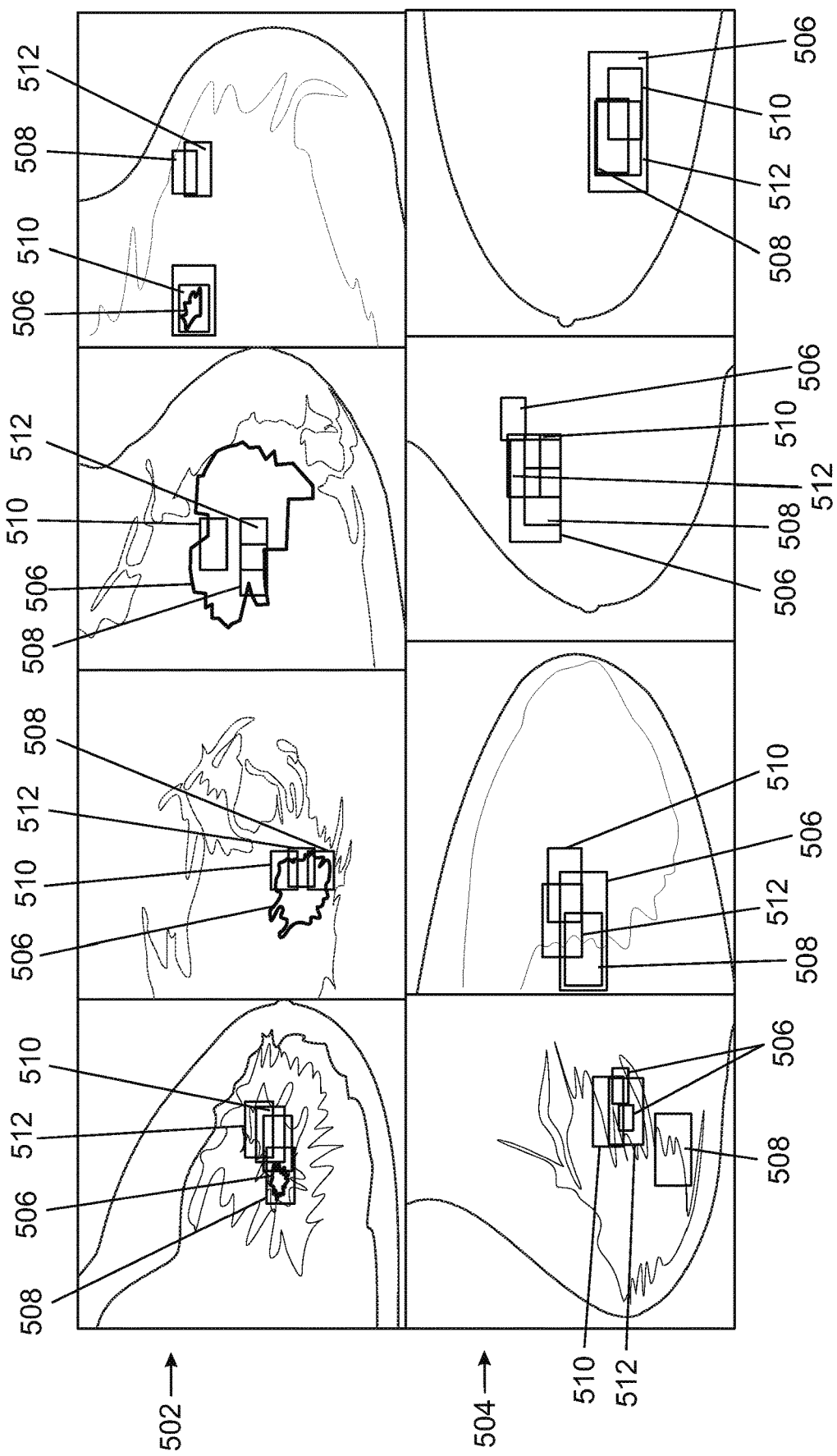
FIG. 5 includes examples of true positive results obtained by the deep CNN during the first experiment described herein, in accordance with some embodiments of the present invention.

Reference is now made to FIG. 5 depict examples of true positive results obtained by the deep CNN during the first experiment described herein, in accordance with some embodiments of the present invention. The top row of images (pointed to by arrow 502) are examples from the IMG images. The bottom row of images (pointed to by arrow 504) are examples from the INbreast images. Ground truth annotation is depicted in a contour or rectangle denoted as 506. The three highest ranking patches (in terms of descending order of probability) are marked by rectangles 508, 510, and 512. It is noted that the predicted patches overlap with the ground truth, indicating that the trained deep convolutional neural network correctly identified the location of indication of abnormality within the mammographic image. The results further show the successful localization of the abnormal findings in the mammographic image, whether the abnormality is a tumor or subtle micro-calcifications.

Detection performance via patch saliency cannot be measured in a straight-forward manner. The systems, methods, apparatus, and/or code instructions described herein allow classification of patches according to network probability output and a notion of local saliency may be obtained from the presence or aggregation of discriminative patches. The first image patches indicate the location of the abnormalities to be used for further analysis. It is noted that the localization is obtained without having any local labels in the training set.

The systems, methods, apparatus, and/or code instructions described herein were implemented in MATLAB using the Matconvnet library, providing average running time per image of 4.15 and 0.003 sec for the VGG-M and the neural network respectively.

A second experiment was conducted based on a data set of mammographic images collected at a large multi-center hospital, referred to herein as IMG-2. The data set included 2,500 FFDM from a BI-RADS distribution of 1317, 662, 333 and 47, 141 corresponding to findings in the images associated with maximum BI-RADS 1, 2, 3 and 4, 5 respectively. The mammograms contain various findings such as masses, macro and micro-calcifications.

In a first scenario, the mammograms were divided into the following two labels, BI-RADS 4, 5, 6 as positive (98 cases) and BI-RADS 1, 2, 3 as negative (780 cases). All types of suspiciously malignant abnormalities were included in the positive class to distinguish between any severe abnormality from BI-RADS 4, 5 and normal images (BI-RADS:1) as well as the most likely benign findings (BI-RADS:2 & 3). The data split raises a particular challenge as the deep CNN has to discriminate between images with similar types of lesions, such as malignant versus benign masses or different types of micro-calcifications, often ambiguous even for expert radiologists. The first scenario is referred to herein as TS-1.

A second scenario was tested based on the mammographic images available from the INbreast publicly available FFDM data set. The same split according to BI-RADS score was performed on the INbreast images, which provided 100 positive and 310 negative mammograms. Data was split into a first category of BI-RADS 1 versus BI-RADS 2-6, which represents a use case where the system alerts for any abnormalities, even benign abnormalities. The second scenario is referred to herein as TS-2.

The performance assessment was carried out with 5 fold patient-wise cross-validation. At each train and test iteration, all the images from the patient under test were strictly excluded from the training set, to avoid data contamination and over-fitting.

The results of the second experiment that include the first and second scenario are summarized in Table 2, which presents binary classification performance measured by AUC for different methods with the associated test scenario. The tested methods are differentiated by the type of labeling (Weakly vs. Fully), source and the size (# images) of the data set. The results shown depict two different test scenarios—TS-1: BIRADS 1, 2, 3 vs. 4, 5, 6, and TS-2: BIRADS 1 vs. Rest. For comparison, three reference methods are evaluated: the Self-TL method described with reference to HWANG S., KIM H.-E.: *Self-transfer learning for weakly supervised lesion localization. In International Conference on Medical Image Computing and Computer-Assisted Intervention (MICCAI)* (2016) Springer, pp. 239-246, the Naïve-TL method described with reference to SULAM J., BEN-ARI R., KISILEV P.: *Maximizing auc with deep learning for classification of imbalanced mammogram datasets. In Euro graphics Workshop on Visual Computing for Biology and Medicine* (2017), and the ResNet MG method described with reference to DHUNGLE N., CARNERIO G., BRADLEY A. P.: *Fully automated classification of mammograms using deep residual neural networks. In IEEE International Symposium on Biomedical Imaging* (2017). It is noted that the deep CNN described herein obtains comparable performance to the fully supervised method in Dhungle et al on the same data set and same test scenario.

The Naïve-TL method is based on a naïve transfer learning strategy in which the image (after cropping the area of the breast) is resized to 224×224 pixels. The breast image is then run through an off-the-shelf deep CNN model, trained on the Imagenet dataset, obtaining from a VGG-M model a 4096 long representation vector for the entire image. These features are then used to train an SVM in order to classify them as positive or negatives. Note that this reference demonstrates the impact of image significant downsizing on the AUC.

TABLE 2

| Method-ology | Labels | TS | Data set | Type | # Images | AUC |
|---|---|---|---|---|---|---|
| As described herein | Weakly | 1 | IMG | FFDM | 2500 | 0.831 +/− 0.044 |
| As described herein | Weakly | 1 | INB | FFDM | 410 | 0.722 +/− 0.089 |
| As described herein | Weakly | 2 | IMG | FFDM | 2500 | 0.817 +/− 0.031 |
| As described herein | Weakly | 2 | INB | FFDM | 410 | 0.790 +/− 0.093 |
| Self-TL | Weak | 2 | MIAS | Scanned | 322 | 0.675 |
| Naïve-TL | Weak | 1 | INB | FFDM | 410 | 0.602 |
| ResNet MG | Fully | 1 | INB | FFDM | 410 | 0.740 +/− 0.020 |

The area under the ROC curve (AUC) measure for performance assessment due to the high imbalance distribution between classes in the first and second scenarios. Only 7.5% of mammograms in the IMG set are positive in TS-1. The deep CNN described herein produced an average AUC of 0.831+/−0.044 on the IMG data set in test scenario TS-1. On average, 48% of the false positives are from BI-RADS 2 & 3 categories. These results indicate that many network errors may be associated with wrong classification of masses and calcifications, which often pose a challenge even for expert radiologists. Testing on the small data set of INB resulted in a lower AUC of 0.722+/−0.089. The lower AUC associated with high STD in INB reflects the influence of the small data size, on learning capability and validation. Note that for the commonly used 5-fold cross validation, there are approximately 16 positive images in each fold (only about 8 patients).

The results indicate that the Self-TL method yields an AUC measure of 0.675, a significantly lower performance on a similar size data set as INB, yet on a scanned MG set. With respect to the fully supervised learning method of ResNet MG tested on INB, the deep CNN described herein achieves comparable result on the same data set when considering a single MG, but without requiring local annotations. The Naïve-TL demonstrates the significant impact of strongly downsizing the image resulting AUC of 0.602 on INB. Note that the deep CNN described herein is further capable of distinguishing between different types of abnormalities such as micro-calcifications which can appear in both classes in TS-1.

Figure 6A:
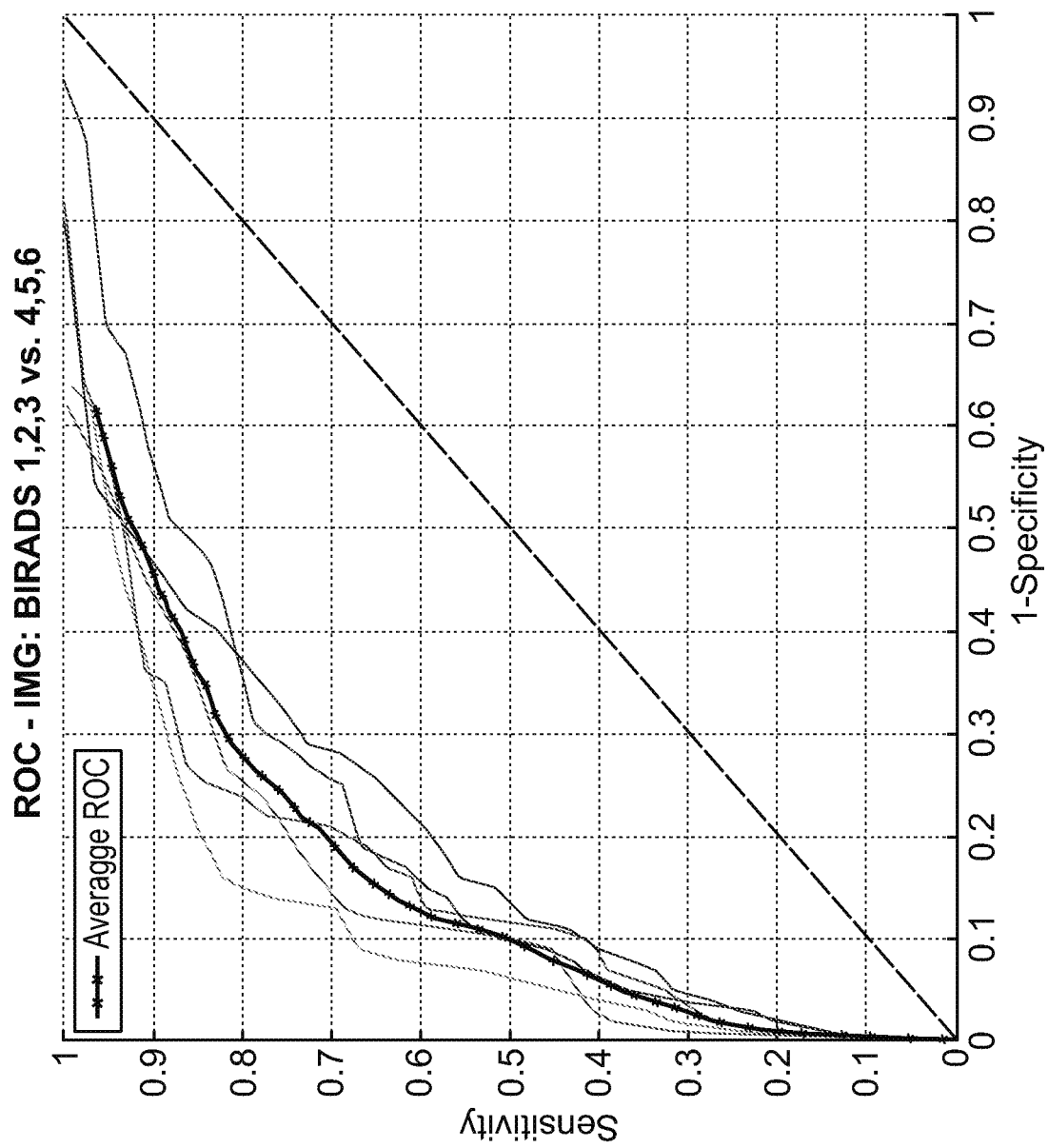
FIG. 6A is an ROC curves for the first case of the second experiment, in accordance with some embodiments of the present invention.

Reference is now made to FIG. 6A, which is an ROC curves for the first case of the second experiment, in accordance with some embodiments of the present invention. The ROC curve of FIG. 6A indicates that for TS-1 with highly probable malignant MG classification, specificity is 60% @ 87% sensitivity or specificity of 40% @ 96% sensitivity.

Figure 6B:
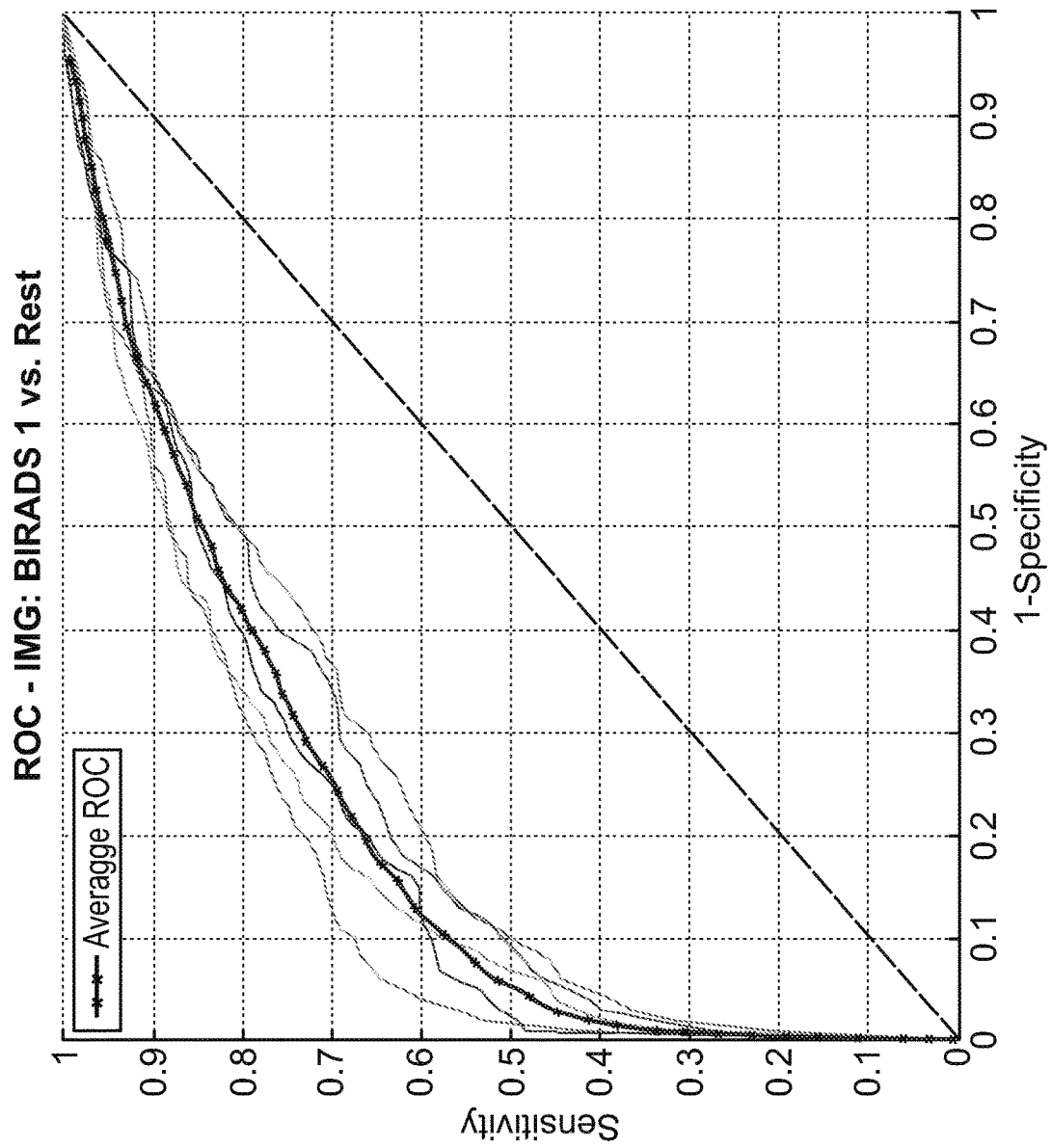
FIG. 6B is an ROC curves for the second case of the second experiment, in accordance with some embodiments of the present invention.

Reference is now made to FIG. 6B, which is an ROC curves for the second case of the second experiment, in accordance with some embodiments of the present invention. The ROC curve of FIG. 6B indicates that for BI-RADS 1 vs. Rest the results are specificity 60% @ 79% sensitivity or specificity 20% @ 96% sensitivity.

The deep CNN classifies each patch according to its discrimination power in separating positive and negative bags. As described herein, the instance score may be used to visualize the discriminating regions that may be referred to as abnormalities. Lesions in the training data set present a large scale variability of over 10 scale factor. Yet the patches extracted for feeding into the deep CNN described herein are at fixed size and aim to alert for a suspicious finding, rather than exact segmentation of the lesion. Therefore, a less strict measure is used for localization rather than standard intersection over union. Considering a symmetric overlap ratio allows a small patch within a large mass to be determined as true. Consequently, it is desired that an extremely large finding is covered by a single or several patches. Considering all top K=5 patches, those having over 50% overlap with a true finding (or symmetrically if 50% of the lesion is covered by a patch) are considered as true positive patches, for localization. Accordingly, two false positive measures are defined for localization derived from patches with an intersection ratio below 50%. The first measure FD is the average false positive (detection) per-image (FPPI) in TP class and FT, commonly used in the literature presenting the average false positive detection per image with respect to all the images in the cohort. At a work point of FD=1 FPPI the deep CNN described herein for the IMG data set in TS-1 yields an average recall rate of R=0:76 @ FT=0:48. This means that on 76% of TP images at least one lesion is accurately localized by the deep CNN described herein, while keeping the total FPPI below 0.5.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant mammographic images will be developed and the scope of the term mammographic image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for training a deep convolutional neural network (CNN) for detecting an indication of likelihood of abnormality in a target anatomical image based on a plurality of anatomical training images each associated with an annotation for a whole respective training image, comprising:
   receiving the plurality of anatomical training images, each including an associated annotation indicative of abnormality for the whole respective anatomical training image without an indication of a location of the abnormality within the respective anatomical image;
   executing, for each respective anatomical training image of the plurality of anatomical training images:
      decomposing the respective anatomical training image into a plurality of patches;
      computing a feature representation of each patch of the plurality of patches;
      computing for each respective patch of the plurality of patches, according to the feature representation of the respective patch, a probability that the respective patch includes an indication of abnormality;
      setting a probability indicative of likelihood of abnormality in the respective anatomical image according to the maximal probability value computed for one patch of the plurality of patches; and
   training the deep convolutional neural network for detecting the indication of likelihood of abnormality in the target anatomical image according to the plurality of patches of the plurality of anatomical training images, the one patch, and the probability set for each respective anatomical training image;
   wherein the deep CNN is trained according to a loss function that computes a log likelihood loss according to a probability that a certain patch of the plurality of patches is classified as indicative of abnormality based on a plurality of coefficients of the deep CNN; and
   wherein the loss function is mathematically represented as:

$$\mathcal{L}(\theta) = \sum_{\substack{X_i \in \Lambda \\ Y_i = y_+}} \log\left(\max_{x_{ij} \in X_i} \mathbb{P}(y_+ \mid x_{ij}, \theta)\right) + \sum_{\substack{X_i \in \Lambda \\ Y_i = y_-}} \log\left(1 - \max_{x_{ij} \in X_i} (\mathbb{P}(y_+ \mid x_{ij}, \theta))\right)$$

wherein:
   $x_{ji}$ denotes the respective patch of the respective anatomical image,
   $\theta$ denotes the coefficients of the deep CNN,
   $\mathbb{P}(y+\mid x_{ij}, \theta)$ denotes a probability that the respective patch denoted $x_{ji}$ is classified as positive based on the coefficients $\theta$ of the deep CNN.

2. The method according to claim 1, wherein an abnormality appearing in each one of the plurality of anatomical training images is not associated with a manual annotation indicative of location of the abnormality within the respective anatomical training image.

3. The method according to claim 1, wherein the loss function considers the one patch of the plurality of patches most probably indicative of abnormality and excludes other patches of the plurality of patches with lower probability values than the one patch, wherein the one patch is back propagated through the deep CNN for updating of the coefficients of the deep CNN.

4. The method according to claim 3, wherein the probability comprises a probabilistic geometric prior value denoting areas on a border of at least one tissue portion based on distance from an edge of the area on the border of the at least one tissue portion.

5. The method according to claim 4, wherein the geometric prior value is mathematically represented as:

$$\omega(x_{ij}) = 1 - \frac{\mathcal{A}(x_{ij} \cap \mathcal{B})}{\mathcal{A}(x_{ij})}$$

where:
$\omega(x_{ji})$ denotes the geometric prior value,
$\mathcal{A}(x_{ij})$ denotes the area of the respective patch of the respective anatomical image $x_{ij}$, and
$\mathcal{A}$ denotes the area on the border of the at least one tissue portion.

6. The method according to claim 1, wherein the size of each of the plurality of anatomical training images is at least one of arbitrary and varying between each of the plurality of anatomical training images, and wherein a number of the plurality of patches is at least one of arbitrary and varying between each of the plurality of anatomical training images.

7. The method according to claim 1, wherein the respective anatomical training image is decomposed based on a sliding window moved within the respective anatomical training image to extract each of the plurality of patches, wherein the each patch of the plurality of patches overlaps with at least one other patch of the plurality of patches.

8. The method according to claim 1, wherein the plurality of patches are decomposed from the respective anatomical training image in full resolution and without downsampling.

9. The method according to claim 1, wherein the trained deep CNN comprises a first stage including a pretrained CNN, wherein trained deep CNN coefficients are extracted from a last hidden layer of the pretrained CNN, and a second stage comprising a refined fully connected neural network comprising three fully connected layers trained from scratch according to a loss function that considers the one patch of the plurality of patches and back propagates the one patch through the refined fully connected neural network.

10. The method according to claim 9, wherein the trained deep CNN coefficients extracted from the last hidden layer of the first stage are represented as a 4096D feature vector, wherein the feature representation of each patch comprises the 4096D feature vector.

11. The method according to claim 10, wherein the refined fully connected neural network computes for each respective patch of the plurality of patches, according to the corresponding feature vector, the probability that the respective patch includes an indication of abnormality.

12. The method according to claim 9, wherein the convolutional neural network coefficients extracted from the last hidden layer of the first stage are computed once for each patch of the plurality of patches.

13. The method according to claim 9, wherein the three fully connected layers of the refined fully connected neural network comprise rectified linear units (ReLUs) as non-linear layers, and wherein the second stage is optimized using momentum stochastic gradient descent.

14. The method according to claim 1, wherein the plurality of anatomical training images comprise a plurality of mammographic training images, each including at least one breast portion.

15. A computer implemented method for detecting an indication of likelihood of abnormality in a target anatomical image, comprising:
receiving the target anatomical image;
decomposing the target anatomical image into a plurality of patches;
computing a feature representation of each patch of the plurality of patches by a deep CNN trained based on a plurality of anatomical training images each associated with an annotation for a whole respective training image without an indication of a location of the abnormality within the respective anatomical image;
computing by the deep CNN, for each respective patch of the plurality of patches, according to the feature representation of the respective patch, a probability that the respective patch includes an indication of abnormality; and
setting a probability indicative of likelihood of abnormality in the target anatomical image according to the maximal probability value computed for one of the plurality of patches;
wherein the deep CNN is trained according to a loss function that computes a log likelihood loss according to a probability that a certain patch of a plurality of patches of the anatomical training images is classified as indicative of abnormality based on a plurality of coefficients of the deep CNN; and
wherein the loss function is mathematically represented as:

$$\mathcal{L}(\theta) = \sum_{\substack{X_i \in \Lambda \\ Y_i = y_+}} \log\left(\max_{x_{ij} \in X_i} \mathbb{P}(y_+ | x_{ij}, \theta)\right) + \sum_{\substack{X_i \in \Lambda \\ Y_i = y_-}} \log\left(1 - \max_{x_{ij} \in X_i} (\mathbb{P}(y_+ | x_{ij}, \theta))\right)$$

wherein:
$x_{ji}$ denotes the respective patch of the respective anatomical training image,
$\theta$ denotes coefficients of the deep CNN,
$\mathbb{P}(y+|x_{ij},\theta)$ denotes a probability that the respective patch denoted $x_{ji}$ is classified as positive based on the coefficients $\theta$ of the deep CNN.

16. The method according to claim 15, further comprising providing an indication of a location indicative of likelihood of abnormality according to the location with the target anatomical image of at least one patch of the plurality of patches associated with the maximal probability value.

17. The method according to claim 16, further comprising presenting on a display, the target anatomical image with a plurality of overlay markings each indicative of the location of one of the plurality of patches within the anatomical image according to decreasing probability values, wherein each overlay marking distinctly represents a descending order of probability, wherein each overlay indicates abnormality location in full resolution.

18. A system for training a deep CNN for detecting an indication of likelihood of abnormality in a target anatomical image based on a plurality of anatomical training images each associated with an annotation for a whole respective training image, comprising:
a non-transitory memory having stored thereon a code for execution by at least one hardware processor of a computing device, the code comprising:
code for receiving the plurality of anatomical training images, each including an associated annotation indicative of abnormality for the whole respective anatomical training image without an indication of a location of the abnormality within the respective anatomical image;
code for executing, for each respective anatomical training image of the plurality of anatomical training images:

decomposing the respective anatomical training image into a plurality of patches;

computing a feature representation of each patch of the plurality of patches;

computing for each respective patch of the plurality of patches, according to the feature representation of the respective patch, a probability that the respective patch includes an indication of abnormality;

setting a probability indicative of likelihood of abnormality in the respective anatomical image according to the maximal probability value computed for one patch of the plurality of patches; and code for training a deep convolutional neural network for detecting the indication of likelihood of abnormality in the target anatomical image according to the plurality of patches of the plurality of anatomical training images, the one patch, and the probability set for each respective anatomical training image;

wherein the deep CNN is trained according to a loss function that computes a log likelihood loss according to a probability that a certain patch of a plurality of patches of the anatomical training images is classified as indicative of abnormality based on a plurality of coefficients of the deep CNN; and wherein the loss function is mathematically represented as:

$$\mathcal{L}(\theta) = \sum_{\substack{X_i \in \Lambda \\ Y_i = y_+}} \log\left(\max_{x_{ij} \in X_i} \mathbb{P}(y_+ \mid x_{ij}, \theta)\right) + \sum_{\substack{X_i \in \Lambda \\ Y_i = y_-}} \log\left(1 - \max_{x_{ij} \in X_i} (\mathbb{P}(y_+ \mid x_{ij}, \theta))\right)$$

wherein:

$x_{ji}$ denotes the respective patch of the respective anatomical training image, $\theta$ denotes coefficients of the deep CNN, $\mathbb{P}(y+x_{ij},\theta)$ denotes a probability that the respective patch denoted $x_{ji}$ is classified as positive based on the coefficients $\theta$ of the deep CNN.

* * * * *